United States Patent [19]

Henion et al.

[11] Patent Number: 4,861,988
[45] Date of Patent: Aug. 29, 1989

[54] ION SPRAY APPARATUS AND METHOD

[75] Inventors: John D. Henion, Trumansburg, N.Y.; Thomas R. Covey, Houston, Tex.; Andries P. Bruins, Leek, Netherlands

[73] Assignee: Cornell Research Foundation, Inc., Ithaca, N.Y.

[21] Appl. No.: 103,056

[22] Filed: Sep. 30, 1987

[51] Int. Cl.⁴ .............................................. B01D 59/44
[52] U.S. Cl. ................................ 290/288; 250/281; 250/282
[58] Field of Search ................... 250/288, 288 A, 281, 250/282

[56] References Cited

U.S. PATENT DOCUMENTS 4,160,161 7/1979 Horton ............................ 250/288 A
4,298,795 11/1981 Takeuchi et al. ............... 250/288 A
4,531,056 7/1985 Labowsky et al. ............. 250/288 A
4,607,163 8/1986 Mizuno ........................... 250/288 A
4,730,111 3/1988 Vestal et al. .................... 250/288 A Primary Examiner—Carolyn E. Fields
Assistant Examiner—John A. Miller
Attorney, Agent, or Firm—Laff, Whitesel, Conte & Saret

[57] ABSTRACT

A device for interfacing between a microbore liquid chromatograph and a mass analyser. In such a device, liquid from the liquid chromatograph is sprayed through a stainless steel capillary tube into the atmospheric pressure ionization chamber of a mass spectrometer. A voltage of e.g., plus or minus 3 KV is applied to the stainless steel tube, and a nebulizing gas, e.g. nitrogen, is directed at high velocity past the tube tip through another tube encircling the stainless steel tube. The combination of the nebulizing gas and the electric potential disperses the liquid at room temperature into a fine mist providing an increased and more stable ion signal without thermal decomposition of the compounds being analysed.

17 Claims, 2 Drawing Sheets

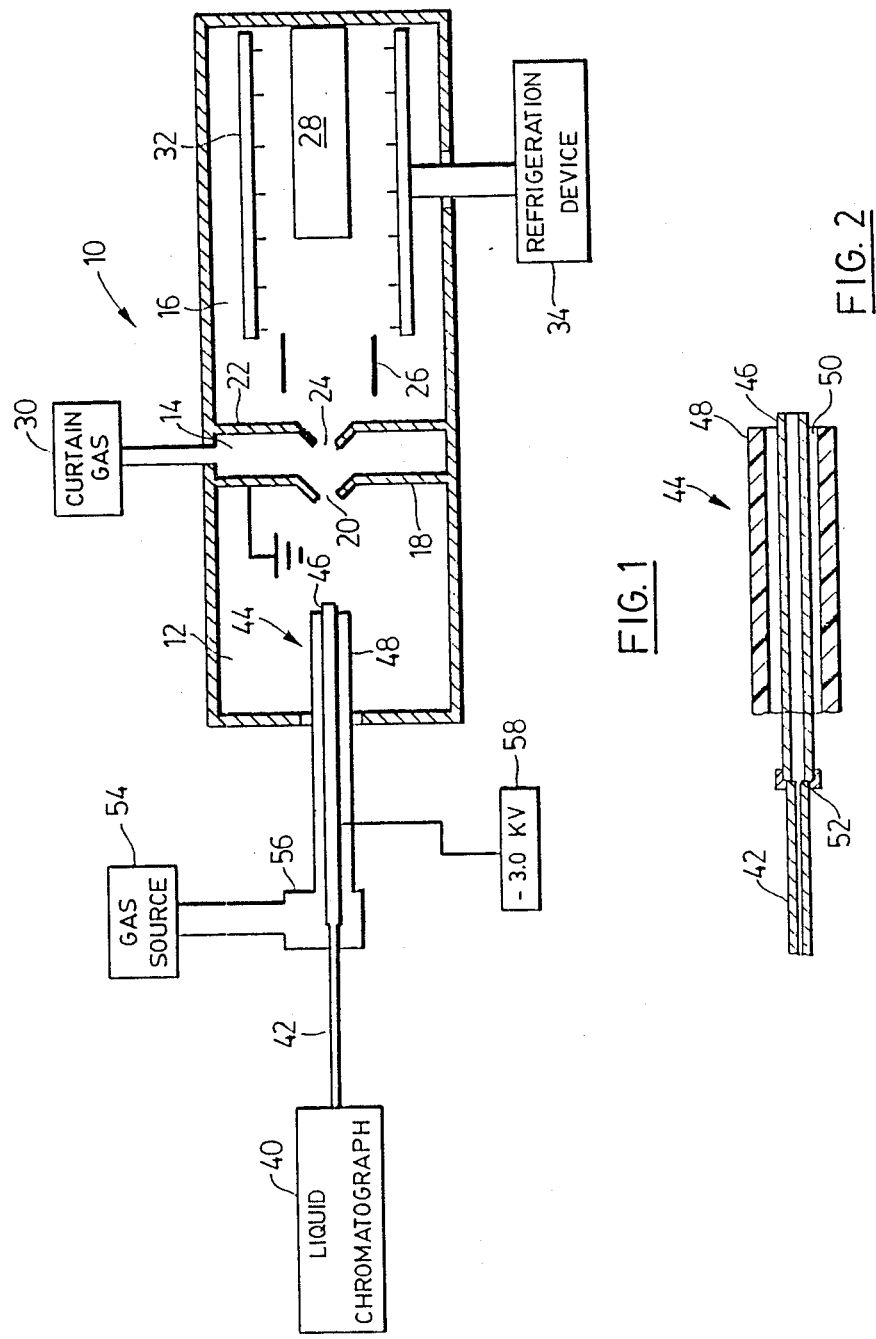

ION SPRAY APPARATUS AND METHOD

FIELD OF THE INVENTION

This invention relates to method and apparatus for forming ions from a liquid, typically liquid from a liquid chromatograph, and for directing such ions into a mass analyser such as a mass spectrometer.

BACKGROUND OF THE INVENTION

Microbore liquid chromatographs are commonly used in the analysis of trace compounds, to provide a degree of separation between the trace compound to be analysed and the other compounds present in the mixture under investigation. The eluent from the liquid chromatograph, after the separation has occurred, is normally subjected to analysis to identify the trace compound or compounds of interest.

It is commonly desired to analyse the liquid from a liquid chromatograph in a mass analyser such as a mass spectrometer. However, since mass spectrometers require an input in the form of free ions, it is usually necessary to evaporate the liquid from the liquid chromatograph, and to produce ions during or after the vaporization process.

One classical method which was commonly used was to spray the liquid from the liquid chromatograph onto a moving belt, which moves into a vacuum chamber where the belt was heated from below. The resultant vapor was then ionized by appropriate means. Another classical method was to spray large droplets from the liquid chromatograph into a heated ion source, so that the droplets were vaporized (typically by contact with the walls of the ion source and by exposure to the instrument vacuum). Both these methods use substantial heat, and this has severe disadvantages. The heat causes thermal decomposition of the compounds in question, and in addition, since the liquid from the liquid chromatograph often contains ammonium ions, these ions often cause ammonium chemical ionization to occur. The thermal decomposition and the ammonium chemical ionization create complexity in the final mass spectrum, making the analysis process more difficult.

To reduce the above difficulties, three alternative more modern methods have been developed for introducing the liquid from a liquid chromatograph into a mass analyser. In one method, referred to as ion evaporation, liquid is sprayed at atmospheric pressure into a chamber in front of the vacuum chamber orifice for the mass analyser. The spray is directed across the orifice into a 90 degree elbow tube. This removes large droplets. The finer portion of the spray is removed less quickly, and since the small droplets therein carry a charge impressed by an electric field which is applied between the sprayer and an induction electrode, ions are released therefrom as the droplets evaporate. Such ions are driven toward the orifice by a deflector electrode. Although this method can accommodate relatively large flows (e.g. 1 milliliter per minute), the method is not particularly sensitive, partly because much of the sample is unused. Thus, the ion current from compounds of interest is very low in this method.

The second relatively modern method which has been developed is referred to as thermospray. In this method, the flow of liquid from the conventional liquid chromatograph passes through a capillary, the end of which is heated to between 200 and 350 degrees C. The resultant vaporization results in a spraying process, which is usually into a low pressure chamber but can be into an atmospheric pressure chamber. Contrary to the ion evaporation process, the droplets formed are charged not by an electric field, but rather by statistical fluctuations in the distribution of ions in solution when the liquid is dispersed into an aerosol. As the charged droplets evaporate, ions are released therefrom. Thermospray is relatively effective in producing a fine mist and currently is commonly used. However, a substantial disadvantage of the process is that again, some thermal decomposition occurs, even though not all of the liquid is directly subjected to heating. In addition, again some unwanted ammonium chemical ionization may occur. Therefore, while the temperatures used can be carefully controlled by a microprocessor, nevertheless, thermospray is commonly recognized as being a "fussy" process which may give good results one day and poor results another. In addition, in practice some workers report that thermospray is generally less sensitive for ionic compounds (i.e. compounds which form ions in solution) then is the ion spray technique.

The third process which has been developed to produce ions from the liquid of a small bore liquid chromatograph, and to introduce such ions into a mass analyser, is the so-called electrospray technique. In this technique, liquid from the liquid chromatograph is directed through a capillary tube the end of which is connected to one pole of a high voltage source. The end of the capillary tube is spaced from the orifice plate through which ions travel into the mass analyser vacuum chamber. The orifice plate is connected to the other pole of the high voltage source. The electric field generates charged droplets, producing a liquid flow without a pump, and the droplets evaporate to produce ions. Electrospray can be carried out without a pump (in which case the flow is 1 to 2 microliters per minute) or with a pump.

The electrospray method has several disadvantages. Firstly, it can handle only a very small flow, typically only up to about 10 microliters per minute. Faster pumping produces larger droplets, causing the ion signal to fall off and also to become unstable. Secondly, the high voltages needed to disperse a larger liquid flow into fine droplets tend to create an electrical or corona discharge. The discharge adds complexity to the spectrum produced by the mass analyser, causing difficulties in interpretation, and in addition, for unknown reasons, it tends to suppress the ion signal from the evaporated droplets. A further disadvantage is that the electrospray method is very sensitive to the position of the end of the capillary tube relative to the orifice plate.

In addition, the electrospray method requires that the proportion of water in the liquid be low, since otherwise a stream of large droplets tends to be produced. The large droplets reduce the sensitivity (i.e. the ion signal) and also affect the stability of the ion signal, i.e. large fluctuations occur in the ion signal.

SUMMARY OF THE INVENTION

The invention in one of its aspects provides improved apparatus for forming ions from a liquid and for introducing such ions into a mass analyser. In its broadest aspect the present invention provides apparatus for forming ions from a liquid and for introducing said ions into a mass analyser, comprising:

(a) an inner capillary tube to receive said liquid and having a first free end, (b) an outer tube encircling said inner capillary and defining therewith a narrow annular space therebetween, said outer tube having a second free end located substantially at said first free end, (c) means for directing a flow of gas through said annular space at a high velocity, (d) an orifice plate having an orifice therein, said tubes being located on one side of said orifice plate with said free ends spaced therefrom, (e) a mass analyser on the other side of said orifice plate for receiving ions passing through said orifice plate, (f) and means for creating an electric field between said first free end and said orifice plate, whereby the combination of said electric field and said gas flow past said free end of said inner conductive tube produces a mist of fine charged droplets of said liquid, so that said charged droplets may evaporate and release ions therefrom.

In another aspect, the invention provides a method of forming ions from a liquid and for introducing said ions into a mass analyser, comprising:

(a) directing said liquid through a conductive capillary tube having a free end, (b) directing a high velocity annular jet of air past said free end in the direction of flow of said liquid, (c) generating an electric field between said free end and an orifice plate for said ions, the combination of said jet of air and said electric field acting to produce a mist of charged droplets and to produce ions from said droplets, (d) and guiding said ions through said orifice into a mass analyser located beyond said orifice.

Further objects and advantages of the invention will appear from the following description, taken together with the accompanying drawings.

BRIEF DESCRIPTION OF THE DRAWINGS

In the accompanying drawings

FIG. 1 is a diagramatic view of apparatus according to the invention;

FIG. 2 is a diagramatic view of a capillary tube and sheath used in the FIG. 1 apparatus.

DETAILED DESCRIPTION OF PREFERRED EMBODIMENT

Figure 3:
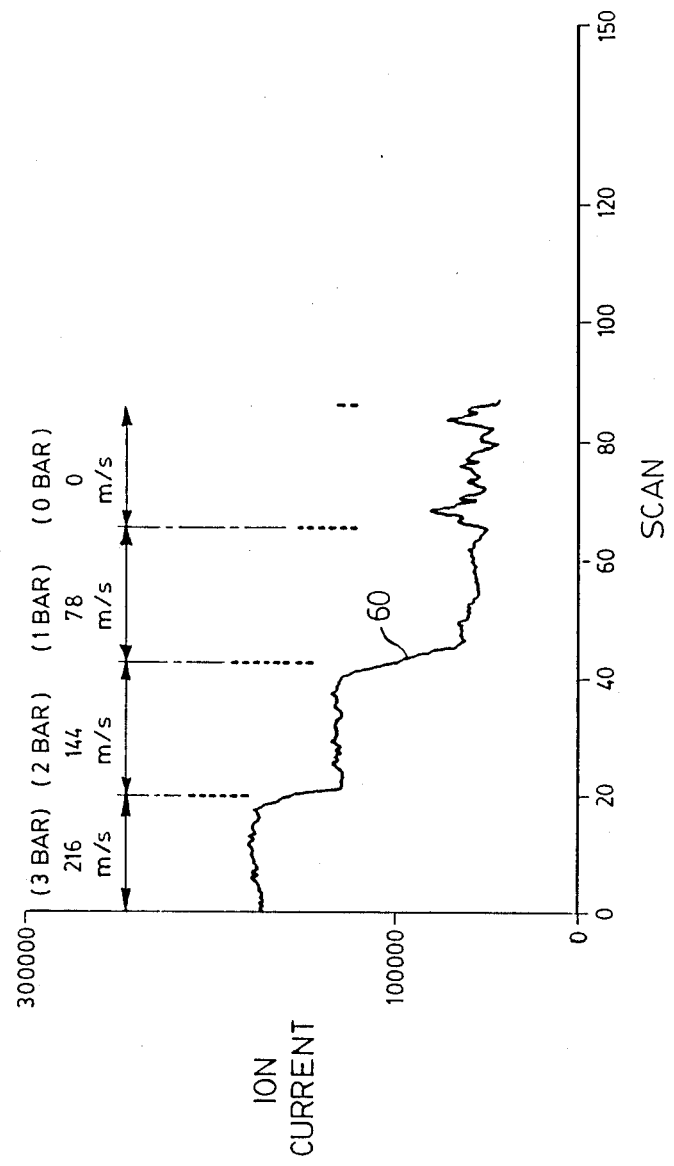
FIG. 3 is a graph showing ion current with various gas velocities.

Reference is made to the drawings, which show diagramatically at 10 a typical mass spectrometer instrument. The instrument 10 is typically that sold by Sciex Division of MDS Health Group Limited of Thornhill, Ontario, Canada, under its trade mark TAGA 6000. The instrument 10 includes an atmospheric pressure ionization chamber 12, a gas curtain chamber 14 and a vacuum chamber 16. The ionization chamber 12 is separated from the gas curtain chamber 14 by an inlet plate 18 containing an inlet orifice 20. The gas curtain chamber 14 is separated from the vacuum chamber 16 by an orifice plate 22 containing an orifice 24.

In use, the sample to be analysed is introduced into the ionization chamber 12 and is ionized as will be described. The ions are drawn by an electric field through the inlet opening 20, through the orifice 24, and are focused by a lens 26 into a tandem triple quadrupole mass spectrometer 28.

In order to prevent gases from the ionization chamber 12 from entering the vacuum chamber 16, the gas curtain chamber 14 is supplied from a source 30 with a curtain gas (typically nitrogen or argon) at a pressure higher than that prevailing in the ionization chamber 12. Gas from the gas curtain chamber effuses through the orifice 20 into the ionization chamber 12 and also passes through the orifice 24 into the vacuum chamber 16. In the TAGA instrument described, the vacuum is produced by cryopumping, i.e. the nitrogen, argon or other curtain gas is condensed on cooling fins 32 which are cooled by a refrigeration device 34.

According to the invention, liquid from a small-bore liquid chromatograph 40 flows through a thin quartz tube 42 into a device 44 best shown in FIG. 2 and which will be referred to as an "ion spray" device. The ion spray device 44 comprises a stainless steel capillary tube 46 of circular cross-section, encircled by an outer tube 48 also of circular cross-section. The inner diameter of the stainless steel capillary tube 46 is typically 0.1 millimeters, and its outer diameter is typically 0.2 millimeters. The inner diameter of the outer tube 48 is typically 0.25 millimeters, leaving an annular space 50 between the two tubes of thickness 0.025 mm. The outer diameter of the outer tube 48 is not critical and the outer tube 48 can be made of any desired thickness depending on the material from which it is formed. Typically the outer tube 48 is made of the plastic sold under the trade mark TEFLON TM. Normally, the tip of the stainless steel tube 46 protrudes slightly from the outer tube 48.

Typically the quartz tube 42 from the liquid chromatograph 40 will be 0.050 mm inner diameter. The tube 42 is sealed at its end 52 to the stainless steel tube 46, so that the liquid flowing in the tube 42 can expand into the stainless steel tube. The stainless steel tube 46 is typically about 10 centimeters in length, although this may vary.

A gas, typically nitrogen boiled from liquid nitrogen, is introduced into the space 50 between the tubes 46, 48 from a source 54. The source 54 is connected to the outer tube 48 by a fitting diagramatically indicated at 56, through which the inner quartz tube 42 passes. Other gases, such as "zero air" (i.e. air with no moisture) or oxygen can also be used.

A source 58 of electric potential is connected to the stainless steel tube 46. For negative ion operation, the stainless steel capillary may be kept at $-3000$ volts, and for positive ion operation at $+3000$ volts. The orifice plate 18 is grounded.

Nitrogen from the source 54 was supplied at a pressure of 2.5 bar (i.e. 2.5 atmospheres) into the annular space 50. This produced a high gas velocity through the space 50.

During normal operation, the axis of the stainless steel tube 46 was positioned 5 to 10 millimeters off the axis of the orifices 20, 24, to prevent sampling of large cluster ions. A fine mist or fog was observed emanating from the tip of the tube 46. It was found that the combination of the electric field and the gas flow served to nebulize the liquid stream. The device shown was tested and found effective at flow rates up to 0.2 ml per minute, but it was found that the best sensitivity was obtained at about 40 microliters per minutes, a flow rate which is compatible with 1 millimeter inner diameter packed microbore liquid chromatograph columns.

It was also found that the nebulizer gas flow through the annular space 50 allowed a larger distance to be maintained between the tip of the stainless steel tube 46 and the orifice plate 18 than in the case of ordinary electrospray. This larger distance, together with maintaining the voltage difference between tube 46 and plate 18 at no more than about 3 KV, reduced the electric field at the tip of the tube 46 and prevented a corona discharge, even with nitrogen used as the nebulizing gas. Had pure oxygen been used, this would have reduced the likelihood of a corona discharge even further, since oxygen tends to capture free negative electrons emitted during the spray process. However, the use of oxygen was not found necessary.

It was also found that the best sensitivity was achieved when the tip of the stainless steel tube 46 was positioned three to four centimeters from the orifice plate 18. However, the spray process was relatively independent of the position of the tip of tube 46, i.e. the tip of the tube 46 could be moved over a range of positions without seriously degrading the ion signal.

It will be appreciated that the invention is applicable only for certain compounds. It is primarily applicable for ionic compounds, i.e. compounds which are already ionized in solution. These compounds include many dyes and drugs. In addition, the method is applicable in the case of certain neutral molecules which cluster with ions in solution and remain clustered with the ions during the ion spray process. Examples of such compounds having neutral molecules which cluster with ions are digitoxin and certain estrogens, e.g. diethyl stilbestrol.

The invention has been tested on members of a number of classes of compounds which, when present in very small quantities (and since they are usually accompanied by other compounds) have proven very difficult to detect reliably. The invention has performed surprisingly well on various members of the following classes of compounds:

1. disulfonated azo dies
2. phenolic compounds
3. carboxylic acids
4. various fragile drug compounds (e.g. digitoxin as mentioned, nystatin, and a drug produced by Squibb under its trade mark Aztreonam
5. nucleotides It is found that the use of the invention produces mild ionization (unlike, for example, thermospray which tends to decompose molecules because of the heat involved) and very high sensitivity, resulting in surprisingly good results even when very small quantities of many compounds which are difficult to detect are involved.

The apparatus shown in the drawings was tested by varying the nebulizer gas pressure from source 54, to determine the effect on the ion signal when the gas pressure was varied. The result of this test is shown in FIG. 3, in which scan numbers (scan rate 3 seconds per scan) are plotted on the X axis and the total ion current (shown as counts per second registered on the TAGA instrument used) is plotted on the Y axis. The resultant ion signal curve is indicated at 60. The flow rate chosen for the test was 40 microliters per minute, and the liquid used was a 0.1 ppm solution of PPG 1000 (polypropylene glycol in 80/20 acetonitrile/one millimolar ammonium acetate). The ion source temperature, i.e. the temperature in chamber 12, was 40° C.; the pressure in chamber 12 was atmospheric, and the voltage from source 58 was set at 3 KV. The gas pressure from source 54 was varied between 3 bar and 0 bar (above atmospheric pressure), and the gas velocity through the annular space 50 was measured for each gas pressure.

The annular space 50 in the experiment was 0.025 mm. in thickness and about one cm. long.

In FIG. 3 the gas velocities measured are shown in meters per second (m/s) across the top of the drawing, and the gas pressures which produced those velocities are shown in parentheses above the velocities (in pressures above atmospheric). It will be seen that the ion signal 60 was highest at a gas velocity of 216 m/s, being more than 170,000 counts per second and with little fluctuation. When the gas velocity decreased to 144 m/s, the ion counts decreased to about 130,000 counts per second, still with little background noise. At a gas velocity of 78 m/s, the ion count fell to about 50,000 counts per second, again with a fairly low level of background noise or fluctuation. An ion current of 50,000 counts per second is useable, but with much more difficulty than the higher level recorded at a gas velocity of 216 m/s.

When the gas velocity dropped to zero, the ion current remained at an average level of about 50,000 counts per second, but with a great deal of fluctuation or background noise. It is believed that this was due to the presence of larger droplets which were not dispersed or broken up by the gas stream. The presence of these large fluctuations makes far more difficult the interpretation of the output signal (i.e. the ion count) from the machine. To remove this background noise or random fluctuations in the signal without the gas flow, it would be necessary to reduce the liquid flow rate greatly. This would mean that part of the flow from the liquid chromatograph would have to be discarded, decreasing sensitivity.

Had the electric field applied been higher (by using higher voltage or by moving the tip of tube 46 closer to plate 18), the ion signal would have been greater at lower pressures. However too high an electric field creates a risk of creating a corona discharge.

In general a preferred range of gas velocity past the tip of the tube 46 is between about 140 and 250 meters per second for a liquid flow rate of 40 microliters per minute. A higher flow rate requires a higher gas velocity range. As can be seen from FIG. 3, a relatively high gas velocity produces a very substantial increase in ion signal. While the gas velocity can be lowered if the tip of tube 46 is closer to orifice plate 18, or if a higher voltage or lower liquid flow is used, the velocity is preferably above about 140 meters per second. Too low a velocity causes a reduction in sensitivity, i.e. a reduction of ion signal. However even a lower velocity (e.g. 78 m/s), while it does not increase the ion signal, nevertheless makes the signal much more useable since it reduces random fluctuations in the signal. A gas velocity of 78 m/s is still a high velocity in ordinary terms, since it corresponds to 280.8 kilometers per hour or 174 miles per hour.

The inner diameter of the capillary tube 46 may vary, depending on the application. A diameter of 100 microns (a micron is 0.001 mm) was found suitable. Typically, the inner diameter may range between 25 and 250 microns. In addition, the thickness of the annular space 50 may vary, a preferred thickness being 75 microns and a preferred range being between 50 and 100 microns.

While the description shows the liquid flow into the ion spray device 44 as being from a liquid chromatograph, in suitable circumstances the liquid flow can be injected directly into the ion spray device 44 without a liquid chromatograph column.

It is noted that a high percentage of methanol or acetonitrile in the liquid directed into tube 46 helps the pneumatic dispersion into droplets small enough for the emission of ions. Methanol and acetonitrile have a lower dielectric constant than water and hence allows ions to escape more readily. The presence of ammonium acetate (a common buffer salt) at a concentration of 0.01 M and above strongly reduced the sensitivity for ionic analytes. However, the same concentration of ammonium hydroxide or acetic acid did not have this adverse effect.

It is noted that a high percentage of water in the eluent or sample solution did not impair the performance of the ion spray interface in the tests which were conducted, contrary to the case of the electrospray interface.

The embodiments of the invention in which an exclusive property or privilege is claimed are defined as follows:

1. Apparatus for analyzing ions from trace sample molecules in a liquid comprising:
   (a) a chamber,
   (b) an inner capillary tube to receive said liquid and having a first free end in said chamber for discharging said liquid into said chamber,
   (c) an outer tube encircling said inner capillary tube and defining therewith an annular space therebetween, said outer tube having a second free end located substantially at said first free end, said second free end therefore also being in said chamber,
   (d) means for directing a flow of gas through said annular space for said gas to flow over said first free end and into said chamber at a velocity of substantially at least 50 meters per second,
   (e) an orifice plate having an orifice therein, said tubes being located on one side of said orifice plate with said free ends spaced therefrom, said orifice defining an outlet from said chamber,
   (f) a mass analyser on the other side of said orifice plate, outside said chamber, for receiving ions passing through said orifice plate,
   (g) means for providing the pressure in said chamber to be substantially atmospheric pressure, and the temperature in said inner tube and in said chamber being sufficiently low to avoid thermal decomposition of said trace sample molecules,
   (h) means for creating an electric field between said first free end and said orifice plate, wherein the combination of said electric field and said gas flow past said free end of said inner capillary tube produces a mist of fine charged droplets of said liquid, and wherein said charged droplets evaporate in said chamber and release ions therefrom.

2. Apparatus according to claim 1 wherein said inner tube is formed from an electrically conductive material.

3. Apparatus according to claim 2 wherein said inner tube is a stainless steel tube and said means for generating said electrical field includes means for applying a potential to said stainless steel tube.

4. Apparatus according to claim 2 wherein the inner diameter of said inner tube is of the order of between 0.05 and 0.15 millimeters.

5. Apparatus according to claim 4 wherein the inner diameter of said inner tube is of the order of 0.1 millimeters.

6. Apparatus according to claim 2 wherein the thickness of said annular space is of the order of 0.075 millimeters.

7. Apparatus according to claim 2 wherein said means for directing said flow of gas includes a source of pressurized gas, the pressure of said gas being between 2 and 3 bar.

8. Apparatus according to claim 2 and including a liquid chromatograph for supplying said liquid, said liquid chromatograph having an outlet tube for said liquid flowing therefrom, said outlet tube being of an insulating material and being connected to said inner tube for said inner tube to receive the entire flow from said liquid chromatograph.

9. Apparatus according to claim 8 wherein said gas is nitrogen.

10. Apparatus according to claim 2 wherein said first free end extends slightly beyond said second free end.

11. Apparatus according to claim 2 wherein said means (d) includes means for producing a gas velocity of between about 78 and 250 meters per second through said annular space.

12. Apparatus according to claim 2 wherein said means (d) includes means for producing a gas velocity of between about 140 and 250 meters per second through said annular space.

13. A method of analyzing ions from trace sample molecules in a liquid, comprising:
   (a) directing said liquid through a conductive capillary tube having a free end in a chamber,
   (b) directing an annular jet of gas having a velocity of at least 50 meters per second past said free end in the direction of flow of said liquid,
   (c) maintaining the pressure in said chamber at substantially atmospheric pressure and maintaining the temperature in said tube and in said chamber sufficiently low to avoid thermal decomposition of said trace sample molecules,
   (d) generating an electric field in said chamber between said free end and an orifice plate for said ions, the combination of said jet of gas and said electric field acting to produce a mist of charged droplets and to produce ions in said chamber from said droplets,
   (e) and guiding ions out of said chamber through an orifice in said orifice plate, into a mass analyzer located outside said chamber beyond said orifice plate.

14. The method according to claim 13 wherein the velocity of said jet of gas is in the range between about 78 and 250 meters per second.

15. The method according to claim 13 wherein the velocity of said jet of gas is in the range between about 140 and 250 meters per second.

16. The method according to claim 13 wherein said gas is nitrogen.

17. The method according to claim 13 and including the step of pre-separating components of said liquid in a liquid chromatograph prior to directing said liquid through said capillary tube.

* * * * *

UNITED STATES PATENT AND TRADEMARK OFFICE
CERTIFICATE OF CORRECTION

PATENT NO. : 4,861,988
DATED : 8/29/89
INVENTOR(S) : John D. Henion, Thomas R. Covey and Andries P. Bruins It is certified that error appears in the above—identified patent and that said Letters Patent is hereby corrected as shown below:

In the Specification, as a new first paragraph prior to the Field of Invention, insert:

--This invention was at least in part funded under EPA Grant No. CR-811661-10-0; therefore, the Federal Government has certain rights in the invention.--

Signed and Sealed this

Twenty-second Day of May, 1990

Attest:

HARRY F. MANBECK, JR.

*Attesting Officer*  *Commissioner of Patents and Trademarks*